United States Patent [19]

Foldesy

[11] Patent Number: 5,163,448
[45] Date of Patent: Nov. 17, 1992

[54] CONDOM COMPRISING DISPENSING STRUCTURE, AND METHOD OF MAKING AND USING THE SAME

[75] Inventor: Robin G. Foldesy, Raleigh, N.C.

[73] Assignee: Family Health International, Durham, N.C.

[21] Appl. No.: 693,623

[22] Filed: Apr. 30, 1991

[51] Int. Cl.⁵ ............................................. A61F 6/04
[52] U.S. Cl. ................................... 158/844; 128/918
[58] Field of Search ............................ 128/842–845, 128/832, 157, 834, 830, 831, 833, 917, 918

[56] References Cited

U.S. PATENT DOCUMENTS

| | | | |
|---|---|---|---|
| 1,819,549 | 9/1927 | Fiessler | 128/834 |
| 2,389,831 | 11/1945 | Welsh . | |
| 2,604,092 | 7/1952 | Brown et al. . | |
| 2,670,736 | 3/1954 | Dunkelberger . | |
| 2,904,041 | 9/1959 | Brown . | |
| 3,282,414 | 11/1966 | Penksa | 128/844 |
| 4,004,591 | 1/1977 | Freimark . | |
| 4,100,309 | 7/1978 | Mickus et al. . | |
| 4,232,675 | 11/1980 | Meldahl . | |
| 4,354,494 | 10/1982 | Hogin . | |
| 4,446,860 | 5/1984 | Gutnick . | |
| 4,576,156 | 3/1986 | Dyck et al. . | |
| 4,589,880 | 5/1986 | Dunn | 128/832 |
| 4,664,104 | 5/1987 | Jaicks . | |
| 4,684,490 | 8/1987 | Taller et al. . | |
| 4,726,359 | 2/1988 | Schroeder | 128/844 |
| 4,735,621 | 4/1988 | Hessel . | |
| 4,795,425 | 1/1989 | Pugh | 128/844 |
| 4,855,169 | 8/1989 | Glothlin et al. | 428/35.2 |
| 4,964,416 | 10/1991 | Foldesy et al. . | |
| 4,966,166 | 10/1990 | Leffler . | |

OTHER PUBLICATIONS

U.S. Pat. No. 07/693,550 filed Apr. 30, 1991.

Primary Examiner—Robert A. Hafer
Assistant Examiner—David J. Kenealy
Attorney, Agent, or Firm—Steven J. Hultquist

[57] ABSTRACT

A condom comprising an elongate sheath, which may be of tubular form or alternatively of baggy- or pouch-type, which is rolled or rollable on a roll ring having applied thereto a material such as a lubricant, contraceptive, and/or medicament, and wherein the proximal portion of the condom is provided with openings therein, such that the roll ring can be squeezed on the applied condom to cause exudation of the applied material through the proximal openings of the sheath. The rolled condom comprises a rolled portion circumscribing a distal end portion of the condom, thereby forming a cavity into which a "plug" of suitable material may be disposed, as a reservoir means for containing lubricant, contraceptive, and/or medicament, as well as providing an orientation-indicating means so that the condom is not misapplied to the penis of a wearer. The sheath may be formed of natural latex rubber or synthetic polymeric materials, e.g., thermoplastic elastomeric material. The condom usefully is employed to reduce the risk of transmission of sexually transmittable disease, and as a barrier contraceptive means.

26 Claims, 2 Drawing Sheets

CONDOM COMPRISING DISPENSING STRUCTURE, AND METHOD OF MAKING AND USING THE SAME

BACKGROUND OF THE INVENTION

1. Field of the Invention

This invention relates to condom articles, and methods for making and using same.

2. Description of the Related Art

In recent years, there has been a significant increase in the incidence and spread of sexually transmitted diseases (STD's). This increase in the incidence and rate of transmission of STD's is associated in part with the development of increasingly antibiotic-resistant strains of disease-causing organisms, e.g., those responsible for diseases such as syphilis and gonorrhea, as well as the absence of any effective cure for acquired immunodeficiency syndrome (AIDS).

Against this background, and the recognition that condoms afford a safe, low cost, and generally reliable means for combatting the spread of STD's, including AIDS, in addition to their traditional function as a barrier-type contraceptive device, the use of condoms has substantially increased in recent years.

Concurrently, most condoms are produced from a latex resin via a dipping process in which a cylindrical rounded-end mold is dipped in a resin bath, so that the mold is coated with a thin layer of the latex rubber material. The thickness of the latex coating on the mold is dependent on the viscosity of the latex, and the speed of extracting the mold from the latex bath. Similar latex dipping processes have been employed with suitably shaped molds to form tight-fitting articles such as surgical gloves.

The above-identified latex resin dipping process has been utilized for decades, and yields a generally satisfactory barrier product at reasonable cost.

With the recent spread of AIDS in the general population and the resurgence of condom usage in sexual activities, there has been interest in improving the strength and reliability characteristics of condoms, and of achieving improvements in manufacturing processes and economics for commercial production of condoms.

Structurally, the conventional latex condom comprises a tubular main sheath with a closed distal end and an open proximal end. The open proximal end of the condom may be circumscribingly bounded by a filament of elastic material, to aid in retaining the condom on the penis of a wearer, to demarcate the proximal opening for use of the condom, and to prevent tearing of or damage to the tubular main sheath of the condom during its application and use. To the extent that this elastic filament bears compressively against the circumference of the base of the penis, a further enhanced protection is provided against leakage of seminal fluid and sperm from the condom, and against entry of vaginal exudates or other coital secretions of the other coital partner into the interior volume of the condom containing the penis during sexual activity.

In order to accommodate the sealing and retention function of the elastic filament at the proximal opening of the condom, the elastic filament must be significantly stretched in application of the condom to the penis of the wearer. Thus, the condom is often difficult for the user to don, due to the small size of the condom's proximal opening, and the resistance to stretching of the proximal opening and the bounding filament which is intended to provide a tight fit once the condom is installed on the penis of the wearer.

During their commercial production, condoms made of latex rubber typically are rolled to render them easier to package, store, and apply, relative to unrolled condoms. Although rolling gives the condom a more compact structure, thereby facilitating ease of packaging and storage, the donning of rolled condoms frequently is difficult since the user must stretch the roll apart in the donning operation. Generally the "spreadability" of the rolled condom is made difficult by its tightly compacted character, and the required positioning of the rolled condom on the invariably asymmetric glans of the penis to initiate unrolling.

Further, the roll portion of the condom initially must be grasped with the fingers for application to the glans and unrolling onto the penis. The size of the condom roll is typically sufficiently small, e.g., generally being less than about 3/16 inch in roll diameter, so that it is difficult to grasp the roll with the fingertips and install the condom on the penis. This is particularly true in the case of very thin or form-fitting condoms which are characterized by a very tiny roll. As a result of the small size (diameter) of the roll, the need to utilize the fingers in installation of the condom, and the absence of any good grippability, the fingertips often are tightly pinched onto the roll to gain purchase thereon. This in turn raises the risk of shredding or puncturing of the condom material by the fingernails or otherwise breaking the condom as a result of such pinching or grasping, so that the condom, when subsequently unrolled, has breaks or discontinuities therein which render the condom deficient or even useless for its intended function.

The foregoing deficiencies of manual grippability of the condom and its susceptibility to damage during its installation are further exacerbated when, as is frequently the case, the condom is provided in lubricated condition. Most condoms are provided with a lubricant coating thereon, and such lubrication can render the condom extremely difficult to grasp prior to and during donning thereof.

The problems described above become even more acute when the user of a condom attempts to locate the proximal opening of the condom and to don the condom in darkened or low lighting environments in which it is difficult to visually ascertain the proper alignment of the condom. An inexperienced user, in particular, frequently attempts to unroll the condom in the wrong direction, and this may also occur even in circumstances where visual inspection of the condom is possible. Such misalignment further increases the risk that the condom may be broken or damaged by its mishandling.

An additional problem resulting from an initial attempt to unroll the condom in the wrong direction, before it is unrolled in the proper direction and installed on the penis of a wearer, is that the original mis-orientation brings the condom surface into contact with the glans of the penis, and this "contacted" surface subsequently, when the condom is properly installed, is on the exterior surface of the condom. Such contacted surface portion of the condom thus may bear disease-causing organisms, as well as seminal fluid, thereby creating a risk of disease transmission and contraceptive failure, and thereby obviating the advantages of condom usage.

An additional shortcoming of present condoms in many instances is the inadequacy of lubrication supplied thereon. As mentioned, most condoms are provided with a lubricant coating thereon, with the amount of lubrication being such as to facilitate vaginal penetration but not so much as to be inconvenient or messy to the user. Frequently, particularly during prolonged intercourse, the condom lubrication dries out or is otherwise dissipated, rendering the subsequent coital activity painful for the recipient sexual partner, and creating or increasing the risk of a break or tear in the condom. In other circumstances, couples engaged in coital activity may want or require additional lubrication. A wide variety of personal lubricants is available, but such lubricants are frequently inconvenient or messy to apply.

Although latex rubber materials have been widely used in the fabrication of condoms, and permit an economical manufacture of condoms to be achieved, latex rubber generally has the disadvantage that it is susceptible to oxidation, aging, and temperature, so that the shelf life of latex rubber condoms, particularly in the tropics, is generally less than desired. Further, latex rubber condoms are highly susceptible to breaking in a significant percentage of cases (estimates variously range from about 3% to about 10% or more, depending on the specific latex material employed in a given condom, the manufacture, processing, age, etc. of the condom, and the circumstances of its application and use).

In an effort to remedy these deficiencies, the art has given consideration to the fabrication of condoms from a variety of synthetic polymeric materials. Relative to latex rubber, synthetic polymeric materials afford substantial potential improvement in the strength and stability characteristics of condoms constructed of same.

Robert G. Wheeler U.S. Pat. No. 4,964,416 issued Oct. 23, 1990, discloses condoms formed of thermoplastic elastic materials such as thermoplastic elastomers, e.g., polyurethanes, polyesters, polyethers, polyether block amides, multiblock rubber-based copolymers, and other elastomeric homopolymers and copolymers, as well as non-elastomeric materials such as olefinic homopolymers and copolymers, e.g., ultra-low density polyethylene. The condoms disclosed in this patent may be of generally cylindrical shape, or alternatively may be formed as a baggy-type or pouch-type enclosure, which is wrapped about the penis for use. The baggy- or pouch-type condoms are retained on the penis in relatively looser configuration than are condoms of generally cylindrical shape which closely overfit the penis, and are rolled or pulled onto the penis for use.

Thermoplastic condoms are also variously disclosed in the art, in the following patents and publications: M. F. Dyke U.S. Pat. No. 4,576,156 issued Mar. 18, 1986 (condom formed of thermoplastic polyurethane material, having a generally cylindrical configuration); European patent application No. 0 147 072 published Jul. 3, 1985 in the names of Robert A. Taller, et al (a polyurethane condom formed by dipping of a mandril into a polyurethane prepolymer solvent solution, followed by heat curing on the mold); L. Hessel U.S. Pat. No. 4,735,621 issued Apr. 5, 1988 (a tubular protective (condom-like) device comprising a flexible, thin-walled tube closed at one end and having at an open end a collar-shaped, outwardly extending portion with means for radially stretching the collar or open end, and formed of natural or synthetic polymers including polyethylenes, polyurethanes, and derivatives thereof); and R. Sorkin U.S. Pat. No. 4,955,392 issued Sep. 11, 1990 (condom of elastic film material composed of a vulcanized blend of thermoplastic elastomer with a low modulus polyolefin such as a low-density polyethylene).

Even though, as shown by the above-described publications, condoms of synthetic polymeric materials have been proposed in the art, such condoms have not come into widespread commercial use, despite the technological capability which exists to produce polymeric sheet and film materials in tonnage (commodity) quantities.

A not uncommon occurrence in coital activity, depending on the anatomy of the partners and the type and character of the coital activities involved, is the incidence of abrasive contacts or impacts of the pubic bones of the respective coital partners against one another, which can physically and psychologically detract from the enjoyment of the coital activity. To remedy such occurrences, the coital partners may interpose hands, pillows, cushions, or the like between their respective contacting groin regions, however this is generally unsatisfactory, and may interfere with or eliminate significant penile penetration, resulting in diminished pleasure and satisfaction in the coital activity.

It would therefore be a significant advance in the art to provide a condom article which overcomes the foregoing various deficiencies, and which may be fabricated of synthetic polymeric materials or conventional latex rubber materials.

Relative to the condom articles, and methods of making and using the same which constitute various aspects of the present invention, related art is described below.

D. M. Robichaud U.S. Pat. No. 4,794,920 discloses a birth control device comprising an oversized sheath fitting loosely about the male organ, with a flange about the open end of the sheath for retaining the open end of the device outside the coital recipient partner's body. The sheath is formed of thin flexible impermeable material which is sized to fit loosely about the erect male organ thereby enabling movement of the male organ relative to the sheath during coitus, with the sheath being conformable to the shape of the vagina upon insertion therein.

H. A. Omley U.S. Pat. No. 4,484,918 issued Nov. 27, 1984 discloses a method and tool for applying a urine receptacle snugly on the penis of a wearer. The device comprises an elastic ring which is expanded to slide over the shaft of the penis without contacting it. The elastic ring then is relaxed and caused to return to a normal position, and the funnel-shaped end of a resilient catheter is slid over the penis and ring with the catheter gripping the outside of the ring in a leak-proof manner.

A. J. Conway, et al, U.S. Pat. No. 4,479,910 issued Oct. 9, 1984 describes a male condom catheter comprising a laminated sheath having an inner layer of latex rubber and an outer layer of silicone rubber, with adhesive therebetween. By this arrangement, the adhesive is released as the sheath is unrolled and adheres to the inner layer for adhesive attachment to the penis.

M. P. Poncy, et al, U.S. Pat. No. 4,275,812 issued Jun. 30, 1981, describes a surgical glove package which is stated to facilitate donning of a surgical glove. In the package, the cuff of each surgical glove is contained in a cylindrical ring with the cuff of the glove stretched around the ring to hold the glove open for donning. A bag is provided with its mouth sealed around the ring and enclosing the outer surface of the glove to maintain sterility prior to its use. In the donning operation, the hand is inserted through the ring into the glove and then the cuff of the glove is released from the ring. The ring then is removed from the hand so as to turn the bag inside out as the ring passes over the hand; the bag remains between the hand and the ring as the ring passes over the hand.

M. W. McGlothlin, et al, U.S. Pat. No. 4,855,169 issued Aug. 8, 1989 describes a prophylactic device having a sheath of elastomeric sheet material with a 100% tensile modulus of at least about 200 psi and a thickness of less than about 0.0014 inch. The sheath has an open end and a border containing a resilient material of reduced 100% tensile modulus, relative to the elastomeric sheet material. In this device, the ratio of the thickness of the border to the thickness of the sheath is from about 10 to about 300. The materials disclosed in the patent for the sheath include polyurethane and various other thermoplastic elastomeric materials. The patent discloses that the border may be constituted by a ring which is either bonded, or unbonded to the sheath.

It is an object of the present invention to provide a condom which may be advantageously formed of synthetic polymeric materials as well as conventional latex rubber materials, and which is characterized by greater ease of application to the penis of a wearer, as compared to conventional condoms.

It is another object of the present invention to provide a condom of the foregoing type, which is readily rolled for packaging and storage, in a manner which facilitates the installation of the condom on the penis of a wearer.

It is a further object of the invention to provide a condom fabricated from thin non-elastic polymeric film material, which may be utilized at film thicknesses lower than those heretofore believed feasible.

It is yet another object of the invention to provide a condom comprising means for cushioning and/or stimulation purposes, for enhancement of sexual pleasure of a recipient coital partner.

It is a still further object of the present invention to provide a method of making a condom of the foregoing type.

It is another object of the invention to provide a method of donning a condom which is superior to heretofore known methods.

It is yet another object of the present invention to provide a condom device furnishing selectively enhanced lubrication for coital activity.

Other objects and advantages of the present invention will be more fully apparent from the ensuing disclosure and appended claims.

SUMMARY OF THE INVENTION

In one aspect, the present invention may utilize a condom comprising an elongate sheath having a closed distal end and an open proximal end, which is rolled or rollable on a ring associated with a proximal part of the main sheath, from the proximal end to the distal end to form a generally toroidal roll circumscribing a distal end portion of the sheath, wherein: (i) the ring element has an axial (thickness) dimension and a transverse (width) dimension each of which is at least 0.125 inch; (ii) the thickness of the sheath is from about 0.0004 inch of the roll ring to the thickness of the sheath is in the range to about 0.003 inch; and (iii) the ratio of the transverse width of the roll ring to the thickness of the sheath is in the range of from 350 to 5,000.

Each of the axial and transverse dimensions is suitably at least 0.20 inch, as for example from about 0.20 inch to about 2 inches, preferably from about 0.25 inch to about 1 inch, more preferably from about 0.30 inch to about 0.60 inch, and most preferably from about 0.35 inch to about 0.50 inch.

Preferably, the thickness of the sheath of the condom is from about 0.001 inch to about 0.002 inch.

Preferably, the ratio of the transverse width of the roll ring to the thickness of the sheath has a value in the range of from about 400 to about 2500.

The ring may be formed of a material which is soft and resilient, as for example having a Shore (OO) durometer of less than 60, preferably less than 50, more preferably from about 5 to about 50, and most preferably from about 5 to about 35.

The ring may be formed of a polymeric material, as for example one which is highly plasticized.

Alternatively, the ring may be formed of sponge, or other natural or synthetic material.

As yet another alternative, the ring could be formed as a hollow annular member of flexible, resilient character, which is filled with a suitable medium, e.g., a liquid, gas, soft solid material, or combinations thereof. For example, the hollow annular member may be filled or fillable with a fluid such as air or water.

Another condom structure which may be employed in the practice of the invention relates to a condom of the foregoing type, wherein the toroidal roll defines with the circumscribed distal end portion of the condom a reservoir, and wherein the reservoir contains a material selected from the group consisting of lubricants, bactericides, viricides, fungicides, spermicides, mixtures thereof, and materials having two or more of the functions thereof.

A still further condom structure which may be employed in the practice of the invention relates to a rolled condom of the type described above, wherein the roll forms with the circumscribed distal end portion of the condom a cavity, and wherein a plug element is disposed in the cavity. Such plug element thus is reposed against inner portions of the roll and against the distal end portion of the condom. In this arrangement, the plug element displays an exposed face which may be used as a guide for installation of the condom on the penis of a wearer, since the exposed face of the plug element covers the exterior surface of the distal end portion of the sheath.

Yet another structural aspect that may be employed in the practice of the invention relates to a packaged condom of the type broadly described hereinabove, optionally including the plug element as described in the preceding paragraph.

A broad aspect of the present invention relates to a condom, preferably of a type broadly described above, wherein the proximal end portion of the sheath is provided with openings therein, and the roll ring is formed of a porous material which is impregnable with a lubricant and/or medicament substance. When this condom is unrolled onto the penis of a wearer, the openings in the proximal end portion of the sheath are exposed. Upon imposition of pressure on the porous ring, the substance retained therein is forced outwardly through the openings in the proximal end portion of the sheath for delivery to a selected application locus, e.g., an application locus defined by a zone of coital activity.

Another aspect of the invention relates to a method of forming a condom of the type broadly described hereinabove, comprising: disposing a tubular sheath on a mandril of corresponding size and shape, wherein the thickness of the sheath is from about 0.0004 inch to about 0.003 inch; positioning a roll ring, having an axial dimension and a transverse dimension each of which is at least 0.125 inch, exteriorly on a proximal end portion of the tubular sheath, with the ratio of the transverse width of the roll ring to the thickness of the sheath being in the range of 350 to 5,000; rolling the tubular sheath on the roll ring from the proximal end toward the distal end of the tubular sheath; and removing the rolled condom from the distal extremity of the mandril.

Still another aspect of the present invention relates to a method of installing a condom of the type broadly described hereinabove on a penis, comprising positioning the rolled condom on the glans of the penis so that the condom is reverse rollable onto the penis, and reverse rolling (unrolling) the roll from the distal end portion to the proximal end portion of the sheath, whereby the condom is rolled onto the penis with the ring disposed at the base of the penis at the conclusion of such reverse rolling.

Another aspect of the invention relates to a condom comprising a tubular sheath having a closed distal end and an open proximal end, and defining a sheath wall, wherein a proximal end portion of the sheath comprises a sheath wall of increased thickness relative to the sheath wall of the remaining portion of the sheath.

Other aspects and features of the present invention will be more fully apparent from the ensuing disclosure and appended claims.

DETAILED DESCRIPTION OF THE INVENTION, AND PREFERRED EMBODIMENTS THEREOF

Figure 1:
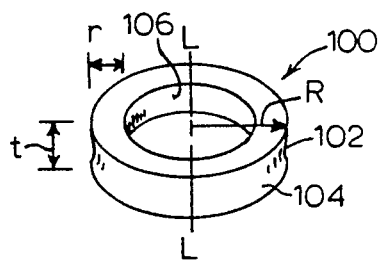
FIG. 1 is a perspective view of a ring element according to one embodiment of the present invention.

In the practice of the present invention, a ring (taken here as referring to an element of ring or toroidal shape, as well as to other functionally equivalent base or core structure) may be employed for rolling of an elongate, e.g., generally tubular, sheath of a condom, to provide enhanced ease of rolling and superior fit in application to the penis of a wearer, wherein: (i) the ring has an axial thickness dimension and a transverse width dimension, each of which is at least 0.125 inch; (ii) the thickness of the sheath is from about 0.0004 inch to about 0.003 inch; and (iii) the ratio of the transverse width of the roll ring to the thickness of the sheath has a value in the range of 350 to 5,000.

As mentioned hereinabove in the "Background of the Invention" section hereof, prior art latex rubber condoms typically employ an elastic filament bounding the proximal end of the condom which typically is less than 1/16 inch in diameter. This filament is employed as the base structure for rolling of the latex rubber condom, e.g., on a mandril, from the proximal end to the distal end thereof, to yield a toroidal roll circumscribing a distal end portion of the condom, wherein the roll typically has a dimension which is between about 1/16 and 3/16 inch in diameter. For example, a Trojan-Enzo ® condom, commercially available from Carter-Wallace, Inc. (New York, N.Y.) has a toroidal roll (in the fully rolled conformation of the condom) which has a diameter of approximately 0.163 inch, in which the elastic filament circumscribing the proximal opening of the condom is approximately 0.080 inch in diameter, and with the toroidal roll comprising approximately 20 wraps or layers in the roll. A Harmony ™ condom, commercially available from Okamoto U.S.A., Inc. (Stratford, Conn.) has toroidal roll comprising 21 wraps or layers, with a diameter of 0.158 inch when the condom is fully rolled, and a diameter of 0.062 inch when unrolled.

By contrast, the condom of the present invention advantageously employs a roll element, i.e., a roll ring, which is substantially greater in size relative to the size (diameter) of the bead or strand employed in prior art latex rubber condoms. By virtue of its larger size, such roll ring yields a smaller number of wraps (layers) in the roll of the fully rolled condom, and provides a substantially larger and grippable roll structure in the rolled condom product. For example, the roll may suitably have a transverse (radial) dimension of about ⅜ inch, and an axial dimension (thickness) of about ½ inch, with 5 wraps or layers in the roll (when the condom is fully rolled). This roll may be formed using a ring having a transverse dimension on the order of 0.35 inch and an axial dimension on the order of 0.40 inch.

Although McGlothlin et al U.S. Pat. No. 4,855,169, discussed hereinabove in the "Background of the Invention" section hereof, describes a prophylactic wherein the ratio of the thickness of the border at the open end of the sheath to the thickness of the sheath is from about 10 to about 300, it has been discovered that such ratio is deficient in various respects. Even at the maximum thickness ratio value disclosed in the McGlothlin et al patent, the transverse dimension of the ring typically is inadequate to provide good purchase to the fingers of a wearer of the condom. By contrast, the relatively larger roll ring described above provides a roll structure whose transverse as well as axial dimensions are substantially better sized to allow ease of donning of positionally and the condom.

Further, relative to the prophylactic described in the McGlothlin et al patent, the condom of the present invention may advantageously employ a relatively larger-sized ring (with respect to the thickness ratio of the ring thickness to the sheath thickness) which provides substantial cushioning and clitoral/labial stimulation which is not provided by the prophylactic disclosed in the McGlothlin et al patent.

Rolling elements (rings) of the aforementioned larger sizes can be employed in connection with the use of oversized, or baggy-type condom sheaths to provide an effective form-fit of the oversized or baggy-type sheath to the penis, in a manner which occludes air from the interior volume between the sheath and the penis, as the condom is being unrolled.

In prior practice, the application of baggy-type condoms or pouches to the penis invariably results in the introduction of air into the interior volume between the condom and the penis. Subsequently, during coital use of the condom, the entrapped air tends to cause undesirable shifting or displacement of the condom on the penis, and in extreme instances results in disengagement of the condom from the penis, and/or the creation of fluidic pressures and stresses within the condom which frequently lead to tearing or breaking of the condom.

Thus, the present invention may utilize baggy-type condoms which are oversized relative to the erect penis on which they are installed, in combination with the use of a flexible, resilient ring (rolling element) which bears compressively against the penis during unrolling of the condom thereon, and causes the condom to assume a close and conforming fit to the penis, particularly when the condom is lubricated and/or constructed of self-adherent material.

An unexpected benefit of such conformal fitting of the oversized condom is that involutions, e.g., creases, folds, ridges, etc., are formed on the applied condom during its installation on the penis, which provide a textured surface which is more closely simulative of the texture of the erect penis than conventional smooth-surfaced, tight-fitting condoms. As a result of this textured surface formation on the applied condom, the resulting sensation and feel of these condoms more closely approaches that which is experienced in the absence of a condom during intercourse.

The elongate sheath forming the main body portion of the condom in the present invention suitably has a thickness of from about 10 to about 70 microns (i.e., from about 0.0004 inch to about 0.003 inch), preferably from about 25 to about 40 microns (i.e., from about 0.001 inch to about 0.0016 inch). Below about 10 microns, the sheath tends to become disproportionately prone to pinhole formation and to possess inadequate thickness to withstand the stresses incident to donning and use of the condom. Above about 70 microns, the sheath becomes too thick to efficiently transmit heat and sensation requisite to the desired use of the condom.

In the preferred practice of the present invention, the roll ring has a transverse width and an axial thickness each of which is at least 0.125 inch, and these transverse width and axial thickness dimensions may for example be from about 0.20 to about 2 inches, preferably from about 0.25 inch to about 1 inch, more preferably from about 0.30 inch to about 0.60 inch, and most preferably from about 0.35 to about 0.50 inch. If the roll ring has transverse width and axial thickness dimensions below 0.125 inch, the physical size of the roll ring tends to be inadequate to obtain good purchase or to achieve rolling and unrolling of the condom with a minimum of wraps or layers of the sheath material on the roll ring. Above about 2 inches, these dimensions become unsuitably large for compact packaging of the condom and tend to interfere with, rather than enhance, coital activity.

The ratio of the transverse width of the roll ring to the thickness of the sheath (wherein the roll ring width and sheath thickness are measured in the same dimensional units), in the preferred practice of the present invention has a value in the range of from 350 to 5,000, and preferably in the range of from about 400 to about 2500. Below the ratio value of 350, the roll ring tends to have insufficient width to provide good purchase and accommodate a minimal number of wraps or layers of the condom in the rolled state. Above a ratio value of 5,000, the transverse width of the roll ring tends to become disproportionately large in relation to the sheath thickness, with the disadvantages noted above in respect of the upper limit of the transverse width and axial thickness dimensions of the roll ring.

Referring now to the drawings, FIG. 1 shows a ring which is suitably employed as a condom rolling element in the practice of the present invention. The ring 100 comprises an annular-shaped body 102 having a cylindrical outer surface 104 and a cylindrical inner surface 106 defining a radial thickness r therebetween. The radial thickness r is a transverse (width) dimension of the ring which may for example be on the order of 0.35 inch, with the radius R of the ring (measured from centerline L—L) being on the order of 0.75 inch. The axial (thickness) t dimension, measured parallel to longitudinal centerline L—L, on the outer cylindrical surface 104, may suitably be on the order of about 0.40 inch, and for a sheath thickness of 25 mils (0.001 inch), the ratio of the transverse width of the ring to the thickness of the sheath is 400.

The ring 100 may be formed of any suitable material of construction which is appropriately sized and sufficiently deformable to permit a condom to be rolled thereon and subsequently to be applied to the penis of a wearer, as hereinafter more fully described. The material of construction for the ring may for example be a natural or synthetic elastomeric material, such as a natural rubber, a synthetic silicone rubber, or a polymer e.g., polyvinylchloride, which has been appropriately plasticized, or swollen by solvent contact, to render the polymer soft and deformable in character. A preferred material of construction of the ring is polyvinylchloride which has been heavily plasticized to impart a gelatinous feel thereto. From the standpoint of conformability to the penis during the application of the rolled condom, the ring rolling element preferably is as elastomeric, i.e., resiliently stretchable in character as possible. The ring material of construction suitably is soft, e.g., having a Shore (00) durometer hardness less than 60, preferably less than 50, more preferably from about 5 to about 50, and most preferably from about 5 to about 35.

Alternatively, the condom may be formed of sponge, or other natural or synthetic material, e.g., polyurethane foam.

It is also within the broad purview of the present invention to form the ring as a hollow annular member of a suitably flexible, resilient material, with the interior volume of the hollow annular ring being filled with any suitable liquid, gas, soft solid, or combination thereof, as appropriate to the specific condom usage. For example, the hollow annular member may be filled, or fillable, with a suitable fluid such as air or water.

The specific form and construction of the ring in a particular application practice of the present invention is readily determinable by those of ordinary skill, without undue experimentation.

FIGS. 2-5 show the application of a rolling ring of the type illustrated in FIG. 1 to a condom mounted on a mandril and rolling of the condom onto the ring and thereafter continuing the rolling from the proximal to the distal end of the condom, to form a rolled condom article.

Figure 2:
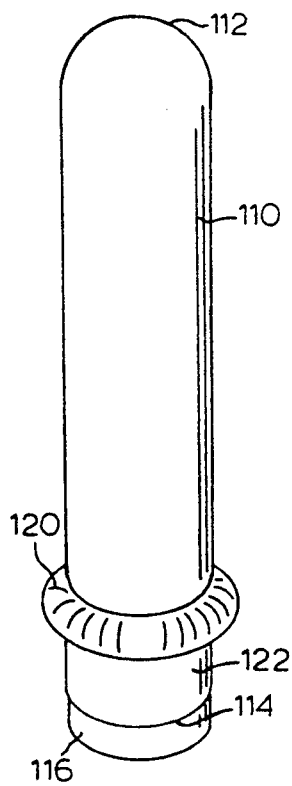
FIG. 2, 3, and 4 are successive perspective views of a condom and rolling ring positioned thereon, as the condom is rolled from the proximal to the distal end thereof, on a mandril.

As shown in FIG. 2, a tubular condom 110 having a closed distal end 112 and an open proximal end 114 is mounted on a mandril 116, so as to conform to the round-ended tubular shape of the mandril.

The rolling ring 120 then is positioned at a proximal end portion 122 of the condom 110, such as by stretching the ring open and placing it on an upper part of the mandril, then translating the ring 120 downwardly from the top to the lower portion of the mandril so that the ring is finally positioned as shown in FIG. 2.

Figure 3:
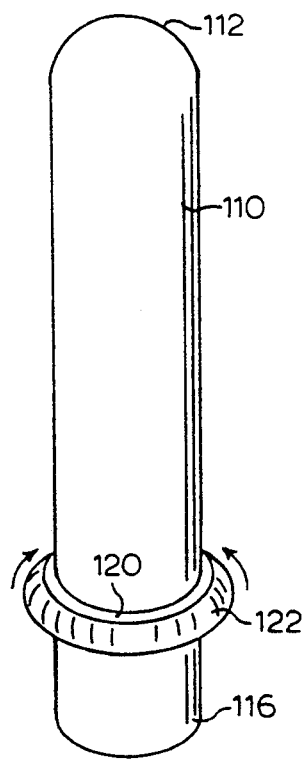
Figure 4:
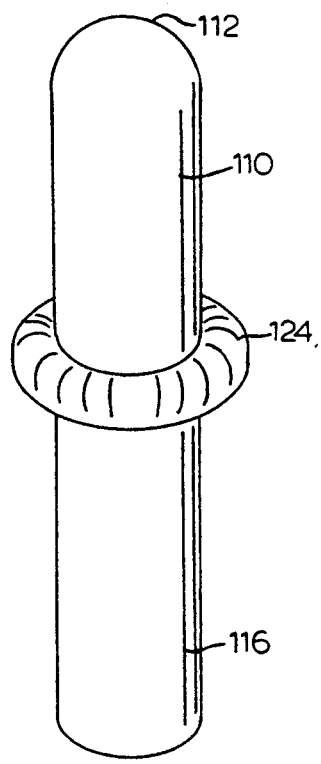

Subsequently, as illustrated in FIG. 3, the proximal end portion 122 of the condom 110 is drawn upwardly over the ring 120, and the condom then is rolled on the ring from the proximal end toward the distal end 112. In this manner, a toroidal roll 124 is formed and grows in size as the condom is rolled thereon toward the distal end of the condom.

Figure 5:
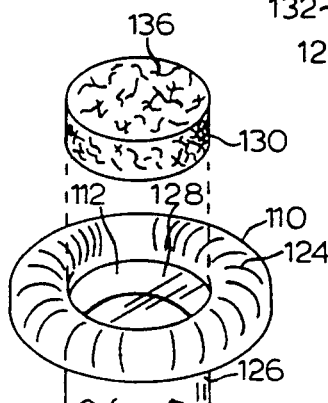
FIG. 5 is a perspective view of a portion of the mandril and condom illustrated in FIGS. 2-4, as the rolled condom is removed from the mandril, showing, in exploded view, a plug element such as may be disposed in the cavity defined by the roll and the distal end portion of the rolled condom.

Finally, at the upper end 126 of the mandril 116, the condom 110 is rolled off the mandril as a fully rolled condom article wherein the toroidal roll 124 circumscribes and defines with the distal end 112 of the condom a cavity or depression 128 (see FIG. 5). This cavity may be employed as a reservoir for lubricant, and/or medicament such as a bactericide, viricide, fungicide, or the like. Alternatively, a mixture of lubricant and medicament may be introduced into the cavity, or a substance having one or more of lubricating, bactericidal, viricidal, and fungicidal characteristics may be introduced thereinto.

Figure 6:
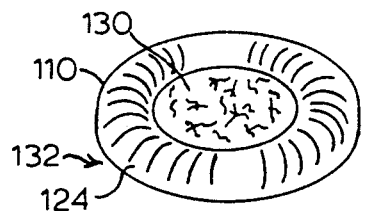
FIG. 6 is a view of a rolled condom comprising a plug element, of the type shown in exploded view in FIG. 5.

As a specific embodiment of the invention, a plug element 130, as shown in the exploded view in FIG. 5, may be inserted into cavity 128, to yield the composite condom device 132 shown in FIG. 6.

The plug element 130 may suitably be formed of a porous material such as sponge, cotton, synthetic (e.g., non-woven) material, compressed cellulose, etc. By virtue of its porosity, the plug element can be impregnated, e.g., saturated, with lubricant and/or medicament materials. In addition, the plug element 130 may be employed to indicate the exterior end of the condom when the condom is to be applied to the penis of a wearer. Thus, the plug element (see FIG. 5) has a circular top surface 136 in the view shown, which is exposed (uncovered) when mounted in the cavity bounded by the toroidal roll 124 of the condom as shown in FIG. 6. The undersurface of plug element 130, opposite surface 136, then is in bearing contact with the distal end portion 112 of the condom.

In this arrangement, the plug element 130 can be formed of a material of construction which has a substantially different texture or "feel," relative to the material of the condom article per se. Accordingly, such different textural character may be employed to provide a tactile identification of the proper orientation of the condom, even in a low-light or no-light environment. Additionally, or alternatively, the plug element 130 may be provided with a distinct or contrasting color relative to the color of the condom 110, e.g., a fluorescent color, to visually indicate the outside end of the condom, so that the condom is placed on the glans of the penis in the proper position, for subsequent unrolling thereon.

Figure 7:
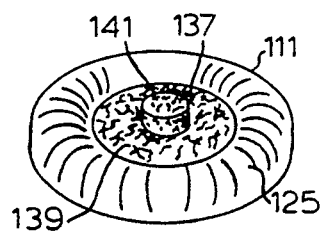
FIG. 7 is a perspective view of a rolled condom according to another embodiment of the invention, wherein the plug element features a grippable protrusion to facilitate its removal from the distal end cavity of the rolled condom.

FIG. 7 shows a modified condom assembly, comprising a condom 111 including a toroidal roll 125 and a plug element 137. In this embodiment, the plug element 137 features on its top surface 139 a manually grippable protrusion 141, by means of which the plug element can readily be withdrawn from the cavity bounded by the toroidal roll 125 of the condom.

Figure 8:
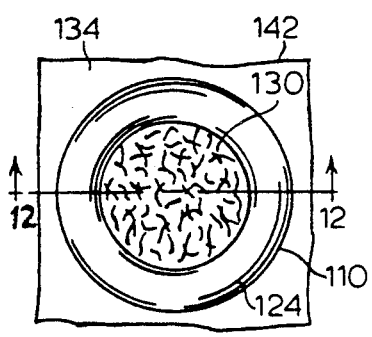
FIG. 8 is a plan view of a condom of the type shown in FIG. 6, disposed in a transparent, sealed package.

FIG. 8 is a top plan view of a condom assembly of the type shown in FIG. 6, disposed in a transparent package 134, such as may be formed of polyethylene, polyurethane, or other suitable package material of construction, with main top and bottom panels which are perimetrally sealed at their edges 142. Alternatively, the condom device may be packaged in a foil or other opaque package, to thereby prevent actinic radiation from penetrating through the packaging material to the condom article, particularly when the condom is constructed of latex rubber or other material which is susceptible to actinic radiation degradation.

Figure 12:
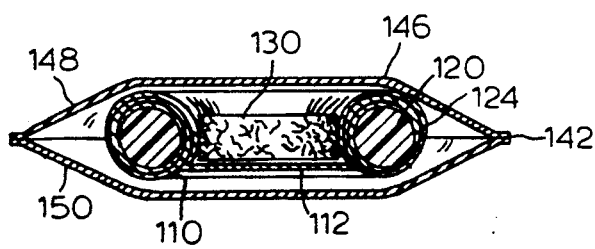
FIG. 12 is a sectional view of the packaged condom article of FIG. 8, taken along line 12—12 thereof.

FIG. 12 is a sectional elevation view of the packaged condom of FIG. 8, taken along line 12—12 thereof. As shown in FIG. 12, the package 146 in which the condom 110 is disposed, comprises an upper panel 148 and a lower panel 150, which are joined to one another at their perimetral edges 142. The condom 110 features toroidal roll 124 comprising multiple layers, or wraps, of main sheath portion of the condom, rolled on the ring 120. The distal end portion 112 of the condom forms with the toroidal roll 124 a cavity in which the plug element 130 is disposed.

Figure 9:
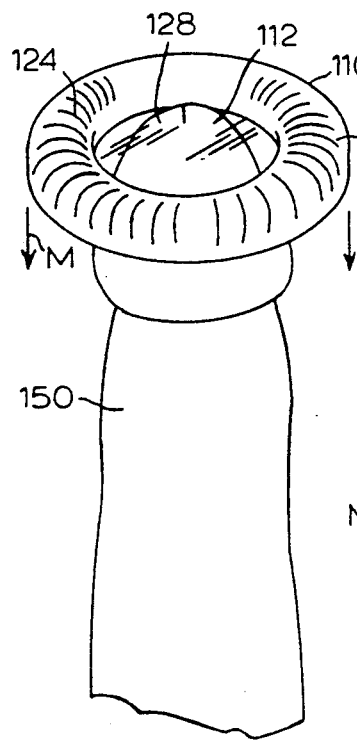
FIG. 9, 10, and 11 show successive views of a rolled condom according to one embodiment of the present invention as it is rolled onto an erect penis.
Figure 10:
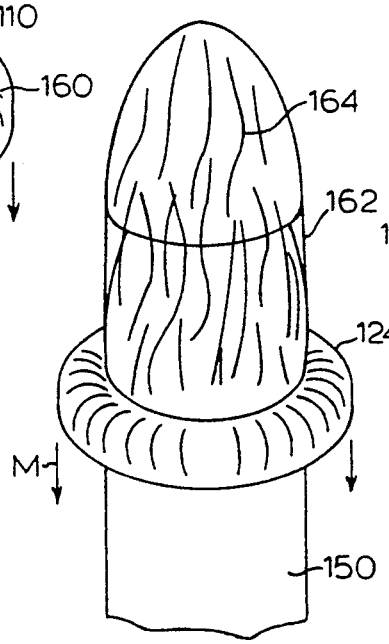
Figure 11:
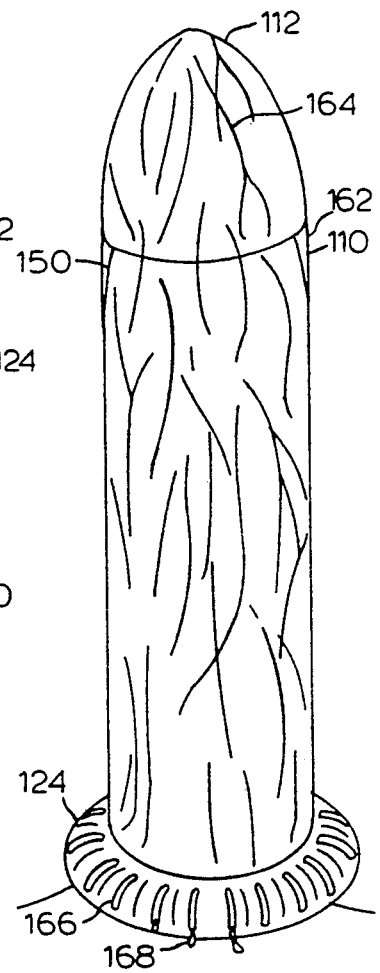

FIGS. 9-11 show the application of a rolled condom in accordance with the present invention, to an erect penis.

As shown in FIG. 9, the condom 110 is disposed on the glans of erect penis 150, with the condom positioned such that the toroidal roll 124 is downwardly unrollable onto the shaft of the penis. In other words, the cavity 128 formed by toroidal roll 124 and distal end portion 112 of the condom is oriented such that the cavity faces outwardly as shown relative to the distal end of the penis.

As the toroidal roll 124 of condom 110 is downwardly translated from the glans of the penis to the base thereof, i.e., in the direction indicated by arrows M in FIGS. 9 and 10, the longitudinal involutions 160 (creases, folds, ridges, and the like), which are present in the roll as a consequence of the substantial size of the rolling ring, subsequently are transferred and/or reformed in the main sheath portion 162 of the condom as installed on the penis, so that the installed condom correspondingly features a number of longitudinal involutions 164 which "texturize" the applied condom with creases, folds, ridges, valleys, and the like, so that the topography of the film forming the main sheath portion 162 of the condom approaches the texture of the skin of the erect penis.

As a result of this texturization of the condom as applied to the penis, the sheathed penis has an enhanced feel of the sheathed penis to both coital partners, which, relative to conventional condoms, more closely approximates the feel and sensation of intercourse in the absence of a condom or other protective barrier means. As a result, the pleasure and satisfaction of coital activity is substantially enhanced.

The enhancement of sexual activity by the texturization of the condom is particularly provided by condoms according to the present invention which are oversized relative to the wearer's penis. Thus, in the unrolling operation, as shown in FIG. 10, the toroidal roll 124 exerts a compressive force against the penis while the main sheath portion 162 of the condom is being downwardly drawn over the erect penis. As a result, an oversized sheath is closely conformed to the shape and size of the penis, with the excess or oversize material resulting in the formation of the aforementioned involutions 164.

The compressive effect of the toroidal ring 124 during application of the condom further serves to occlude air from the interior volume of the condom. This in turn achieves a substantial advance in the use of oversized, e.g., baggy-type or pouch-type, condoms which are otherwise plagued by the introduction of air between the condom and the penis during condom application, which frequently results in bursting or failure of the condom in use.

By minimizing the introduction of air into the interior volume of the condom during its application, the condom of the present invention, when employed in the form of a baggy- or pouch-type device, is able to be used without the occurrence of "hydraulic" failures which otherwise would result from the presence of gross amounts of air between the condom and the penis.

While of value in adapting the oversized (baggy- or pouch-type) condom to the penis of a wearer, the present invention is not thus limited, and extends to the use of sheaths which are form-fitting or otherwise appropriately sized to the penis of the wearer. In any case, however, the substantially larger roll ring which preferably is utilized in the condom of the present invention, relative to the proximal opening bead or strand structures of prior art condoms, results in the formation of the aforementioned involutions 160 in the toroidal roll 124 of the condom as initially formed and rolled (see FIG. 9) and corresponding involutions in the condom sheath when the condom is applied to the penis.

The condoms of the present invention may be formed of any of a wide variety of materials of construction, including thermoplastic or other synthetic polymeric materials, both elastic and non-elastic in character, and including latex rubber or other natural materials, as well as blends, composites, and combinations of any of such materials with one another.

FIG. 11 shows a condom 110 which has been fully unrolled onto the erect penis 150, resulting in a reduced-sized toroidal roll 124 at the base of the penis, and with the main sheath portion 162 of the condom featuring texturizing involutions 164 along its entire length as shown. The condom may optionally have a reservoir tip at its distal end portion 112, as is well known in the art, or may comprise the smooth-tipped structure shown in the drawing of FIG. 11.

As a specific feature which may be employed in condoms of the present invention, the ring 120 (see FIGS. 2 and 12) may be formed of a porous resilient material such as sponge, porous rubber, or other suitable material, and may be impregnated, prior to rolling of sheath 162 thereon, with a lubricant and/or medicinal material, e.g., lubricants, contraceptives (e.g., spermicides), bactericides, viricides, fungicides, as well as mixtures thereof, with the impregnated material being in the form of a fluid which can be squeezed out of the ring material upon compression thereof.

Concurrently, the proximal portion of the condom sheath may be provided with a series of openings 166 therein, so that when the condom is unrolled on the penis, the toroidal roll 124 at the base of the penis features the ring circumscribed by layer(s) of the distal sheath material which have such openings 166 therein, as shown in FIG. 11. By this expedient, the fluid material 168 contained in the ring may, by manual compression of the toroidal roll 124, or by compression incident to coital activity, be released or exuded through the openings 166, as shown in FIG. 11.

By this structure at the proximal portion of the condom, the toroidal roll 124 of the condom as installed on the penis may for example be squeezed to cause the exudation of (additional) impregnated lubricant when needed in the course of coital activity, or the openings may be provided in sufficient number and size to effect continuous "weeping" of the fluid material from the ring through the openings 166 to the locus of coital activity. In such manner, lubricant can be provided throughout coital activity. Correspondingly, intermittent or continuous application can be affected, as desired, of medicaments or contraceptives to the locus of coital activity.

Another feature of the condom of the present invention relates to the provision of the toroidal roll 12 at the base of the penis when the condom is applied, so that the roll serves as a muff or collar of soft material which not only cushions the pelvic contacts of the coital partners (which otherwise, depending on the vigor of the coital activity, may cause discomfort), but also may effect stimulation of the labia and/or clitoris of the female coital recipient, resulting in enhanced pleasure and satisfaction during intercourse.

Although the invention has been illustratively described hereinabove with reference to use of a rolling ring of separate and discrete character relative to the sheath of the condom which is rolled thereon, it will be recognized that the rolling ring, or other enhanced size rolling means, may be integrally secured at the proximal end portion of the condom. Thus, the rolling ring may be a separate and unattached element of the condom, as shown with reference to FIGS. 2-4, or alternatively, the rolling ring may be secured to the proximal end portion of the condom, such as by adhesive bonding, ultrasonic welding, etc.

Figure 14:
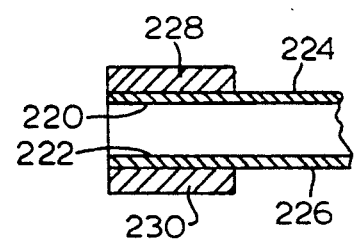
FIG. 14 is a sectional elevation view of a portion of a condom according to another embodiment of the present invention, in which the proximal end exterior wall surfaces have deposited thereon a coating or layer of additional thickness, as a "nucleus" or base structure for rolling of the condom.
Figure 13:
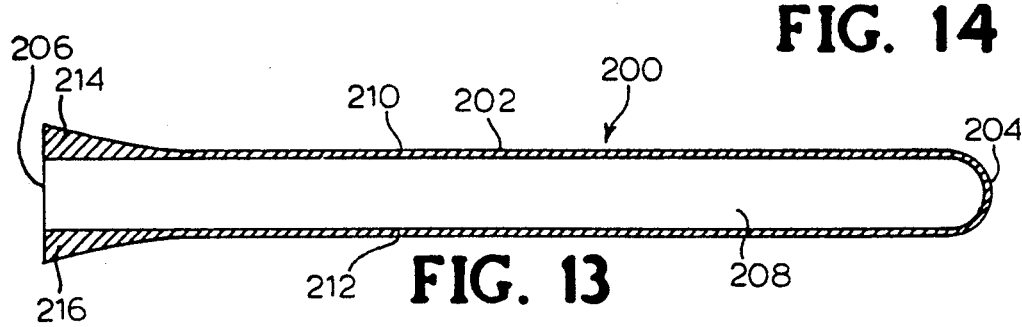
FIG. 13 is a sectional elevation view of a condom according to another embodiment of the present invention, featuring a proximal end portion having increased wall thickness.

Alternatively, the sheath of the condom may be provided with an integrally formed rolling ring or rolling core structure, as shown in FIGS. 13 and 14.

Referring to FIG. 13, there is shown, in sectional view, a condom 200 comprising an elongated sheath 202 having a closed distal end 204 and an open proximal end 206. The condom thereby defines an enclosed interior volume 208, bounded by the walls 210 and 212 of sheath 202. The walls 210 and 212 at their proximal ends 214 and 216, respectively, are of axially progressively thickened character, as shown in the drawing. By such increased film thickness of the sheath wall at the proximal part of the condom, the condom when rolled, such as on a mandril 116 (see FIGS. 2-4) will form a toroidal (i.e., ring-shaped) roll of greater size than is employed in conventional condoms featuring only a small filament strand bounding the proximal end opening of the condom.

The condom shown in FIG. 13 can be suitably formed in a dipping operation, e.g., when the condom is otherwise formed by dipping a mandril or form into a liquid material such as a latex bath, by reversing the mandril and subjecting the condom to additional dipping steps which build up thickness at its proximal end as shown.

Alternatively, the proximal portions 220 and 222 of sheath walls 224 and 226, respectively, may be coated by flow coating or other suitable techniques to form exterior plateaus 228 and 230 thereon, as shown in FIG. 14. In this manner, a rolling "core" structure may be applied to the outer circumferential surface of the sheath at the proximal part thereof. The core thereafter serves as a "nucleus" for rolling, by means of which a roll of enhanced size characteristics, in accordance with the present invention, is readily provided.

As an alternative to the use of proximal sheath openings 166 such as are shown in FIG. II, the rolling ring or rolling core structure may be dosed or otherwise impregnated with the desired lubricant, contraceptive, or medicament material, so that same migrates through the sheath material while the condom is packaged. For example, it may be useful to dose the rolling ring of a condom of the type shown in FIGS. 1–10 with a contraceptive species such as nonoxynol-9, which also is known to have some viricidal activity, so that the nonoxynol-9 migrates through the sheath material during the time that the condom is in the package prior to its use.

As discussed hereinabove, the present invention encompasses the use of such oversized sheaths, as well as of baggy- or pouch-type sheath configurations, to provide a texturized film when applied to the penis, as described in connection with FIGS. 10 and 11. When oversized sheath articles are employed, it may be desirable to utilize a lubricating material, or a low-tack adhesive material on the sheath surfaces, particularly the inner surfaces, to facilitate the conformance of the sheath to the size and shape of the penis.

It will be recognized that the rolling element of condoms of the present invention may have any suitable shape, as suitable to the condom product, and its packaging and use. For example, the rolling element may have the annular ring shape shown in FIG. 1, which by virtue of the resilient character of its material of construction assumes a rounded-ring shape in the rolled condom, as shown in the cross-sectional view of FIG. 12. Alternatively, the rolling element may have the wedge-type structure shown in FIG. 13, or the block-type structure shown in FIG. 14.

Thus, it is not intended that the present invention be limited by the specific rolling element structures and shapes shown, but preferably the condoms of the invention utilize rolling structures which provide an axial thickness (i.e., the thickness in the direction along the longitudinal direction of the elongate sheath, which in the embodiment of FIG. 1 is shown as the axial dimension t), and a transverse width (i.e., the lateral dimension of the ring, perpendicular to the axial or longitudinal direction of the elongate sheath, which in the embodiment of FIG. 1 is shown as transverse dimension r), each of which is at least 0.125 inch. It will be recognized that in some instances, the rolling element may vary in axial thickness and transverse width dimensions over its structural extent, and in such cases the minimal dimension of 0.125 inch is to be imposed on the maximum width or thickness dimensions, or otherwise as appropriate in view of the intents and purpose of the present invention.

As an example of a condom usefully employed in the practice of the present invention, in a specific embodiment thereof, the elongate sheath of the condom may be formed from Elastollan ® thermoplastic polyurethane resin (BASF Corporation (Parsippany, N.J.)) having a thickness of about 25 microns (0.001 inch). The sheath in such embodiment may have a generally tubular shape, with a diameter (measured with the condom in lay-flat position on a planar surface) of 65 millimeters, and with a length of approximately 19 centimeters. The rolling ring may be of a type shown in FIG. 1, constructed of vinyl chloride monomer which has been heavily plasticized and then polymerized to form a low modulus material having a Shore (00) durometer hardness on the order of about 30. This rolling ring may have a diameter (2R, with reference to FIG. 1) which is approximately 1.55 inches, and with an inner opening diameter on the order of 0.75 inch, providing a transverse width r for the ring of approximately 0.40 inch. The axial thickness t of the ring may be approximately 0.375 inch.

While the invention has been described with reference to specific aspects, features, and embodiments, it will be recognized that numerous other variations, modifications, and embodiments are possible, and accordingly all such variations, modifications, and embodiments are to be regarded as being within the spirit and scope of the present invention.

What is claimed is:

1. A condom comprising an elongate sheath of a size and shape for conformal overfitting of a penis along its length, said sheath having a closed distal end and an open proximal end, and at least partially rolled on a roll ring formed of flexible, resilient material having applied thereto a material desirably deployed in the locus of coital activity of the condom, and wherein a proximal portion of the sheath rolled on the roll ring has openings therein of sufficient size, shape, and number to permit passage therethrough of the material applied to the roll ring, upon compression or deformation of the roll ring covered by said proximal portion of the sheath when the condom is applied to the penis of a wearer.

2. A condom according to claim 1, wherein:
the roll ring has a transverse width and an axial thickness each of which is at least 0.12 inch;
the thickness of the sheath is from about 0.0004 inch to about 0.003 inch; and
the ratio of the transverse width of the roll ring to the thickness of the sheath is in the range of from 350 to 5,000.

3. A condom according to claim 2, wherein each of the transverse width and axial thickness dimensions is at least 0.20 inch.

4. A condom according to claim 2, wherein each of the transverse width and axial thickness dimensions is from about 0.20 to about 2 inches.

5. A condom according to claim 2, wherein each of the transverse width and axial thickness dimensions is from about 0.25 inch to about 1 inch.

6. A condom according to claim 2, wherein each of the transverse width and axial thickness dimensions is from about 0.30 to about 0.60 inch.

7. A condom according to claim 2, wherein each of the transverse width and axial thickness dimensions is from about 0.35 to about 0.50 inch.

8. A condom according to claim 1, wherein the thickness of the sheath is from about 0.001 to about 0.002 inch.

9. A condom according to claim 2, wherein the ratio of the transverse width of the roll ring to the thickness of the sheath is in the range of from about 400 to about 2500.

10. A condom according to claim 1, wherein the roll ring is formed of a material having a Shore (00) durometer value of less than 60.

11. A condom according to claim 1, wherein the roll ring is formed of a material having a Shore (00) durometer value of less than 50.

12. A condom according to claim 1, wherein the roll ring is formed of a material having a Shore (00) durometer value of from about 5 to about 50.

13. A condom according to claim 1, wherein the roll ring is formed of a material having a Shore (00) durometer value of from about 5 to about 35.

14. A condom according to claim 1, wherein the roll ring has applied thereto a material selected from the group consisting of lubricants, contraceptive materials, bactericides, viricides, fungicides, and combinations thereof.

15. A condom according to claim 1, in rolled configuration wherein the roll forms with a distal end portion of the sheath a cavity.

16. A condom according to claim 15, wherein the cavity contains a material selected from the group consisting of lubricants, contraceptives, medicaments, and combinations thereof.

17. A condom according to claim 15, wherein a plug is disposed in the cavity.

18. A condom according to claim 17, wherein the plug is provided with a handle, for manual grasping and removal of the plug from the cavity.

19. A condom according to claim 17, wherein the plug is formed of a porous material impregnated with a further material selected from the group consisting of lubricants, contraceptive materials, medicaments, and combinations thereof.

20. A condom according to claim 1, wherein the elongate sheath has a generally tubular shape, with a length which is substantially greater than its diameter.

21. A condom according to claim 1, formed of a material selected from the group consisting of natural latex rubber, synthetic polymeric materials, and mixtures, blends, composites, and combinations thereof.

22. A condom according to claim 1, wherein the elongated sheath is formed of a thermoplastic elastomeric material.

23. A condom according to claim 1, comprising an elongate sheath which is oversized relative to the penis of a wearer thereof, and which has a length which is substantially greater than its diameter.

24. A method of making a condom including an elongate sheath, comprising:
providing a flexible, resilient roll ring having a transverse width and an axial thickness each of which is at least 0.125 inch, with the ratio of the transverse width of the roll ring to the thickness of the sheath being in the range of from 350 to 5,000;
forming an elongate sheath having a closed distal end and an open proximal end, wherein the proximal portion of the sheath has openings therein of sufficient size, shape, and number to permit passage therethrough of material applied to the roll ring, upon compression or deformation of the roll ring when covered by said proximal portion of the sheath;
applying to the roll ring a material desirably deployed at a locus of coital activity of the condom; and
rolling the sheath on the roll ring from a proximal end to the distal end thereof.

25. A method according to claim 24, wherein the elongate sheath is mounted on a mandril, and the roll ring is positioned thereover at a proximal end portion thereof, following which the sheath is rolled on the roll ring.

26. A condom according to claim 1, wherein: the roll element has a transverse width and an axial thickness each of which is from about 0.125 inch to about 2 inches; the thickness of the sheath is from about 0.0004 inch to about 0.003 inch; and the ratio of the axial thickness of the roll element to the thickness of the sheath is from about 400 to about 2500.

* * * * *

UNITED STATES PATENT AND TRADEMARK OFFICE
CERTIFICATE OF CORRECTION

PATENT NO. : 5,163,448
DATED : November 17, 1992
INVENTOR(S) : Robin G. Foldesy

It is certified that error appears in the above-identified patent and that said Letters Patent is hereby corrected as shown below:

Column 14, line 31, after "roll 12" insert --4--.

Column 15, line 21, change "Figure II" to --Figure 11--.

In the claims:

Column 16, line 50, change "0.12" to --0.125--.

Signed and Sealed this

Fourth Day of January, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,163,448
DATED : November 17, 1992
INVENTOR(S) : ROBIN G. FOLDESY

It is certified that error appears in the above-identified patent and that said Letters Patent is hereby corrected as shown below:

In Column 1, after the title, insert

--

The invention claimed herein was made under one or more of the following contracts: U.S. Agency for International Development Contract Nos. DPE-3041-A-00-0043 and DPE-0537-A-00-4047, and National Institutes of Health Contract No. N01-HD-2-3143, and the U.S. government has certain rights therein. --

Signed and Sealed this

Fifteenth Day of November, 1994

Attest:

BRUCE LEHMAN

Attesting Officer

Commissioner of Patents and Trademarks